(12) United States Patent
Ofir

(10) Patent No.: US 10,271,713 B2
(45) Date of Patent: Apr. 30, 2019

(54) TUBED MANIFOLD OF A MULTIPLE VIEWING ELEMENTS ENDOSCOPE

(71) Applicant: EndoChoice, Inc., Alpharetta, GA (US)

(72) Inventor: Yaniv Ofir, Givat Haim Ihud (IL)

(73) Assignee: EndoChoice, Inc., Alpharetta, GA (US)

( * ) Notice: Subject to any disclaimer, the term of this patent is extended or adjusted under 35 U.S.C. 154(b) by 234 days.

(21) Appl. No.: 14/988,551

(22) Filed: Jan. 5, 2016

(65) Prior Publication Data

US 2016/0192822 A1 Jul. 7, 2016

Related U.S. Application Data

(60) Provisional application No. 62/099,846, filed on Jan. 5, 2015.

(51) Int. Cl.
*A61B 1/00* (2006.01)
*A61B 1/012* (2006.01)
(Continued)

(52) U.S. Cl.
CPC .......... *A61B 1/0008* (2013.01); *A61B 1/0011* (2013.01); *A61B 1/00105* (2013.01);
(Continued)

(58) Field of Classification Search
CPC . A61B 1/0008; A61B 1/00071; A61B 1/0089; A61B 1/00101; A61B 1/00137; A61B 1/012; A61B 1/018; A61B 1/00174; A61B 1/00177; A61B 1/00179; A61B 1/00181; A61B 1/00183; A61B 1/00193;
(Continued)

(56) References Cited

U.S. PATENT DOCUMENTS 4,027,697 A 6/1977 Bonney
4,084,401 A 4/1978 Belardi
(Continued)

FOREIGN PATENT DOCUMENTS

CA 2297986 3/1999
CA 2765559 12/2010
(Continued)

OTHER PUBLICATIONS

International Search Report for PCT/US14/37004, dated Sep. 25, 2014.
(Continued)

*Primary Examiner* — Ryan Henderson
(74) *Attorney, Agent, or Firm* — Bookoff McAndrews, PLLC

(57) ABSTRACT

The specification describes a manifold for use in a tip section of a multi-viewing elements endoscope. The manifold has: a first section attached to an elongated second section, where the proximal section has a proximal socket and the distal section has a distal socket; a groove having a first portion along a first axis parallel to a longitudinal axis of the manifold, and a second portion along a second axis tilted at an angle to the first axis; and a working channel tube wherein a distal segment of the tube extends along the first axis to lie within the first portion of the groove, and where a proximal segment of the tube extends along the second axis to lie within the second portion of the groove.

11 Claims, 10 Drawing Sheets

(51) Int. Cl.
  *A61B 1/018* (2006.01)
  *A61B 1/05* (2006.01)
  *G02B 23/24* (2006.01)

(52) U.S. Cl.
  CPC .......... *A61B 1/00193* (2013.01); *A61B 1/012* (2013.01); *A61B 1/018* (2013.01); *A61B 1/05* (2013.01); *A61B 1/051* (2013.01); *G02B 23/24* (2013.01)

(58) Field of Classification Search
  CPC ............ A61B 1/00091; A61B 1/00096; A61B 1/00098; A61B 1/0125; A61B 1/015
  USPC ....... 600/104, 106, 107, 121–125, 127, 129, 600/109–113, 153, 157, 158, 160–182
  See application file for complete search history.

(56) References Cited

U.S. PATENT DOCUMENTS

| | | |
|---|---|---|
| 4,402,313 A | 9/1983 | Yabe |
| 4,461,282 A | 7/1984 | Ouchi |
| 4,494,549 A | 1/1985 | Namba |
| 4,532,918 A | 8/1985 | Wheeler |
| 4,588,294 A | 5/1986 | Siegmund |
| 4,641,635 A | 2/1987 | Yabe |
| 4,727,859 A | 3/1988 | Lia |
| 4,764,001 A | 8/1988 | Yokota |
| 4,801,792 A | 1/1989 | Yamasita |
| 4,825,850 A | 5/1989 | Opie |
| 4,877,314 A | 10/1989 | Kanamori |
| 4,902,115 A | 2/1990 | Takahashi |
| 4,976,522 A | 12/1990 | Igarashi |
| 4,984,878 A | 1/1991 | Miyano |
| 5,007,406 A | 4/1991 | Takahashi |
| 5,014,685 A | 5/1991 | Takahashi |
| 5,193,525 A | 3/1993 | Silverstein |
| 5,224,929 A | 7/1993 | Remiszewski |
| 5,296,971 A | 3/1994 | Mori |
| 5,359,456 A | 10/1994 | Kikuchi |
| 5,395,329 A | 3/1995 | Fleischhacker |
| 5,447,148 A | 9/1995 | Oneda |
| 5,460,167 A | 10/1995 | Yabe |
| 5,464,007 A | 11/1995 | Krauter |
| 5,489,256 A | 2/1996 | Adair |
| 5,518,501 A | 5/1996 | Oneda |
| 5,518,502 A | 5/1996 | Kaplan |
| 5,547,457 A | 8/1996 | Tsuyuki |
| 5,575,755 A | 11/1996 | Krauter |
| 5,587,839 A | 12/1996 | Miyano |
| 5,630,782 A | 5/1997 | Adair |
| 5,662,588 A | 9/1997 | Iida |
| 5,674,182 A | 10/1997 | Suzuki |
| 5,685,823 A | 11/1997 | Ito |
| 5,702,347 A | 12/1997 | Yabe |
| 5,707,344 A | 1/1998 | Nakazawa |
| 5,725,474 A | 3/1998 | Yasui |
| 5,725,476 A | 3/1998 | Yasui |
| 5,725,477 A | 3/1998 | Yasui |
| 5,725,478 A | 3/1998 | Saad |
| 5,777,797 A | 7/1998 | Miyano |
| 5,782,751 A | 7/1998 | Matsuno |
| 5,810,715 A | 9/1998 | Moriyama |
| 5,836,894 A | 11/1998 | Sarvazyan |
| 5,860,913 A | 1/1999 | Yamaya |
| 5,870,234 A | 2/1999 | EbbesmeierneeSchitthof |
| 5,916,148 A | 6/1999 | Tsuyuki |
| 5,940,126 A | 8/1999 | Kimura |
| 6,095,970 A | 8/2000 | Hidaka |
| 6,117,068 A | 9/2000 | Gourley |
| 6,181,481 B1 | 1/2001 | Yamamoto |
| 6,196,967 B1 | 3/2001 | Lim |
| 6,261,226 B1 | 7/2001 | McKenna |
| 6,277,064 B1 | 8/2001 | Yoon |
| 6,359,674 B1 | 3/2002 | Horiuchi |
| 6,375,610 B2 | 4/2002 | Verschuur |
| 6,402,738 B1 | 6/2002 | Ouchi |
| 6,419,626 B1 | 7/2002 | Yoon |
| 6,476,851 B1 | 11/2002 | Nakamura |
| 6,638,214 B2 | 10/2003 | Akiba |
| 6,673,012 B2 | 1/2004 | Fujii |
| 6,712,760 B2 | 3/2004 | Sano |
| 6,832,984 B2 | 12/2004 | Stelzer |
| 6,888,119 B2 | 5/2005 | Iizuka |
| 7,435,218 B2 | 10/2008 | Krattiger |
| 7,621,869 B2 | 11/2009 | Ratnakar |
| 7,630,148 B1 | 12/2009 | Yang |
| 7,701,650 B2 | 4/2010 | Lin |
| 7,713,246 B2 | 5/2010 | Shia |
| 7,746,572 B2 | 6/2010 | Asami |
| 7,813,047 B2 | 10/2010 | Wang |
| 7,828,725 B2 | 11/2010 | Maruyama |
| 7,927,272 B2 | 4/2011 | Bayer |
| 7,967,745 B2 | 6/2011 | Gilad |
| 7,976,462 B2 | 7/2011 | Wright |
| 8,064,666 B2 | 11/2011 | Bayer |
| 8,182,422 B2 | 5/2012 | Bayer |
| 8,197,399 B2 | 6/2012 | Bayer |
| 8,235,887 B2 | 8/2012 | Bayer |
| 8,262,558 B2 | 9/2012 | Sato |
| 8,287,446 B2 | 10/2012 | Bayer |
| 8,289,381 B2 | 10/2012 | Bayer |
| 8,300,325 B2 | 10/2012 | Katahira |
| 8,310,530 B2 | 11/2012 | Bayer |
| 8,447,132 B1 | 5/2013 | Galil |
| 8,449,457 B2 | 5/2013 | Aizenfeld |
| 8,585,584 B2 | 11/2013 | Ratnakar |
| 8,587,645 B2 | 11/2013 | Bayer |
| 8,672,836 B2 | 3/2014 | Higgins |
| 8,715,168 B2 | 5/2014 | Ratnakar |
| 8,797,392 B2 | 8/2014 | Bayer |
| 8,872,906 B2 | 10/2014 | Bayer |
| 8,926,502 B2 | 1/2015 | Levy |
| 9,044,185 B2 | 6/2015 | Bayer |
| 9,101,266 B2 | 8/2015 | Levi |
| 9,101,268 B2 | 8/2015 | Levy |
| 9,101,287 B2 | 8/2015 | Levy |
| 9,314,147 B2 | 4/2016 | Levy |
| 9,320,419 B2 | 4/2016 | Kirma |
| 2001/0036322 A1 | 11/2001 | Bloomfield |
| 2002/0017515 A1 | 2/2002 | Obata |
| 2002/0047897 A1 | 4/2002 | Sugimoto |
| 2002/0087047 A1 | 7/2002 | Remijan |
| 2002/0109774 A1 | 8/2002 | Meron |
| 2002/0161281 A1 | 10/2002 | Jaffe |
| 2002/0172498 A1 | 11/2002 | Esenyan |
| 2002/0183591 A1 | 12/2002 | Matsuura |
| 2003/0030918 A1 | 2/2003 | Murayama |
| 2003/0063398 A1 | 4/2003 | Abe |
| 2003/0076411 A1 | 4/2003 | Iida |
| 2003/0083552 A1 | 5/2003 | Remijan |
| 2003/0128893 A1 | 7/2003 | Castorina |
| 2003/0153897 A1 | 8/2003 | Russo |
| 2004/0015054 A1 | 1/2004 | Hino |
| 2004/0046865 A1 | 3/2004 | Ueno |
| 2004/0061780 A1 | 4/2004 | Huffman |
| 2004/0106850 A1* | 6/2004 | Yamaya ............ A61B 1/00045 600/107 |
| 2004/0133072 A1 | 7/2004 | Kennedy |
| 2004/0138532 A1 | 7/2004 | Glukhovsky |
| 2004/0158129 A1 | 8/2004 | Okada |
| 2004/0160682 A1 | 8/2004 | Miyano |
| 2004/0190159 A1 | 9/2004 | Hasegawa |
| 2004/0249247 A1 | 12/2004 | Iddan |
| 2005/0018042 A1 | 1/2005 | Rovegno |
| 2005/0020876 A1 | 1/2005 | Shioda |
| 2005/0038317 A1 | 2/2005 | Ratnakar |
| 2005/0047134 A1 | 3/2005 | Mueller |
| 2005/0090709 A1 | 4/2005 | Okada |
| 2005/0096501 A1 | 5/2005 | Stelzer |
| 2005/0119527 A1 | 6/2005 | Banik |
| 2005/0234296 A1 | 10/2005 | Saadat |
| 2005/0234347 A1 | 10/2005 | Yamataka |
| 2005/0251127 A1 | 11/2005 | Brosch |

(56) References Cited

U.S. PATENT DOCUMENTS

| | | |
|---|---|---|
| 2005/0272975 A1 | 12/2005 | McWeeney |
| 2005/0283048 A1 | 12/2005 | Gill |
| 2006/0047184 A1 | 3/2006 | Banik |
| 2006/0063976 A1 | 3/2006 | Aizenfeld |
| 2006/0069314 A1 | 3/2006 | Farr |
| 2006/0114986 A1 | 6/2006 | Knapp |
| 2006/0149129 A1 | 7/2006 | Watts |
| 2006/0171693 A1 | 8/2006 | Todd |
| 2006/0173245 A1 | 8/2006 | Todd |
| 2006/0183975 A1 | 8/2006 | Saadat |
| 2006/0184037 A1 | 8/2006 | Ince |
| 2006/0189845 A1 | 8/2006 | Maahs |
| 2006/0215406 A1 | 9/2006 | Thrailkill |
| 2006/0252994 A1 | 11/2006 | Ratnakar |
| 2006/0264704 A1 | 11/2006 | Fujimori |
| 2006/0293556 A1 | 12/2006 | Garner |
| 2007/0015989 A1 | 1/2007 | Desai |
| 2007/0049803 A1 | 3/2007 | Moriyama |
| 2007/0055100 A1 | 3/2007 | Kato |
| 2007/0079029 A1 | 4/2007 | Carlson |
| 2007/0088193 A1 | 4/2007 | Omori |
| 2007/0106119 A1 | 5/2007 | Hirata |
| 2007/0142711 A1 | 6/2007 | Bayer |
| 2007/0162095 A1 | 7/2007 | Kimmel |
| 2007/0167681 A1 | 7/2007 | Gill |
| 2007/0177008 A1 | 8/2007 | Bayer |
| 2007/0177009 A1 | 8/2007 | Bayer |
| 2007/0185384 A1 | 8/2007 | Bayer |
| 2007/0188427 A1 | 8/2007 | Lys |
| 2007/0197875 A1 | 8/2007 | Osaka |
| 2007/0203396 A1 | 8/2007 | McCutcheon |
| 2007/0206945 A1 | 9/2007 | Delorme |
| 2007/0213591 A1 | 9/2007 | Aizenfeld |
| 2007/0229656 A1 | 10/2007 | Khait |
| 2007/0244353 A1 | 10/2007 | Larsen |
| 2007/0244354 A1 | 10/2007 | Bayer |
| 2007/0247867 A1 | 10/2007 | Hunter |
| 2007/0265492 A1 | 11/2007 | Sonnenschein |
| 2007/0270642 A1 | 11/2007 | Bayer |
| 2007/0279486 A1 | 12/2007 | Bayer |
| 2007/0293720 A1 | 12/2007 | Bayer |
| 2008/0021274 A1 | 1/2008 | Bayer |
| 2008/0025413 A1 | 1/2008 | Apostolopoulos |
| 2008/0036864 A1 | 2/2008 | McCubbrey |
| 2008/0045797 A1 | 2/2008 | Yasushi |
| 2008/0058601 A1 | 3/2008 | Fujimori |
| 2008/0071290 A1 | 3/2008 | Larkin |
| 2008/0130108 A1 | 6/2008 | Bayer |
| 2008/0151070 A1 | 6/2008 | Shiozawa |
| 2008/0161646 A1 | 7/2008 | Gomez |
| 2008/0163652 A1 | 7/2008 | Shatskin |
| 2008/0167529 A1 | 7/2008 | Otawara |
| 2008/0177139 A1 | 7/2008 | Courtney |
| 2008/0183034 A1 | 7/2008 | Henkin |
| 2008/0183043 A1 | 7/2008 | Spinnler |
| 2008/0221388 A1 | 7/2008 | Courtney |
| 2008/0253686 A1 | 10/2008 | Bayer |
| 2008/0262312 A1 | 10/2008 | Carroll |
| 2008/0275298 A1 | 11/2008 | Ratnakar |
| 2008/0303898 A1 | 12/2008 | Nishimura |
| 2009/0005643 A1 | 1/2009 | Smith |
| 2009/0023998 A1 | 1/2009 | Ratnakar |
| 2009/0030275 A1 | 1/2009 | Nicolaou |
| 2009/0054790 A1 | 2/2009 | Czaniera |
| 2009/0062615 A1 | 3/2009 | Yamaya |
| 2009/0086017 A1 | 4/2009 | Miyano |
| 2009/0135245 A1 | 5/2009 | Luo |
| 2009/0137875 A1 | 5/2009 | Kitagawa |
| 2009/0143647 A1 | 6/2009 | Banju |
| 2009/0147076 A1 | 6/2009 | Ertas |
| 2009/0182917 A1 | 7/2009 | Kim |
| 2009/0213211 A1 | 8/2009 | Bayer |
| 2009/0216084 A1 | 8/2009 | Yamane |
| 2009/0231419 A1 | 9/2009 | Bayer |
| 2009/0234183 A1 | 9/2009 | Abe |
| 2009/0253966 A1 | 10/2009 | Ichimura |
| 2009/0287188 A1 | 11/2009 | Golden |
| 2009/0287192 A1 | 11/2009 | Vivenzio |
| 2009/0299144 A1 | 12/2009 | Shigemori |
| 2010/0010309 A1 | 1/2010 | Kitagawa |
| 2010/0016673 A1 | 1/2010 | Bandy |
| 2010/0053312 A1 | 3/2010 | Watanabe |
| 2010/0069713 A1 | 3/2010 | Endo |
| 2010/0073470 A1 | 3/2010 | Takasaki |
| 2010/0073948 A1 | 3/2010 | Stein |
| 2010/0076268 A1 | 3/2010 | Takasugi |
| 2010/0123950 A1 | 5/2010 | Fujiwara |
| 2010/0130822 A1 | 5/2010 | Katayama |
| 2010/0141763 A1 | 6/2010 | Itoh |
| 2010/0160729 A1 | 6/2010 | Smith |
| 2010/0174144 A1 | 7/2010 | Hsu |
| 2010/0231702 A1 | 9/2010 | Tsujimura |
| 2010/0245653 A1 | 9/2010 | Bodor |
| 2010/0249513 A1 | 9/2010 | Tydlaska |
| 2010/0280322 A1 | 11/2010 | Mizuyoshi |
| 2010/0296178 A1 | 11/2010 | Genet |
| 2011/0034769 A1 | 2/2011 | Adair |
| 2011/0063427 A1 | 3/2011 | Fengler |
| 2011/0140003 A1 | 6/2011 | Beck |
| 2011/0160530 A1 | 6/2011 | Ratnakar |
| 2011/0160535 A1 | 6/2011 | Bayer |
| 2011/0169931 A1 | 7/2011 | Pascal |
| 2011/0184243 A1 | 7/2011 | Wright |
| 2011/0211267 A1 | 9/2011 | Takato |
| 2011/0263938 A1 | 10/2011 | Levy |
| 2011/0282144 A1 | 11/2011 | Gettman |
| 2011/0292258 A1 | 12/2011 | Adler |
| 2012/0040305 A1 | 2/2012 | Karazivan |
| 2012/0050606 A1 | 3/2012 | Debevec |
| 2012/0053407 A1 | 3/2012 | Levy |
| 2012/0057251 A1 | 3/2012 | Takato |
| 2012/0065468 A1 | 3/2012 | Levy |
| 2012/0076425 A1 | 3/2012 | Brandt |
| 2012/0209071 A1 | 8/2012 | Bayer |
| 2012/0209289 A1 | 8/2012 | Duque |
| 2012/0212630 A1 | 8/2012 | Pryor |
| 2012/0220832 A1 | 8/2012 | Nakade |
| 2012/0224026 A1 | 9/2012 | Bayer |
| 2012/0229615 A1 | 9/2012 | Kirma |
| 2012/0232340 A1 | 9/2012 | Levy |
| 2012/0232343 A1 | 9/2012 | Levy |
| 2012/0253121 A1 | 10/2012 | Kitano |
| 2012/0277535 A1 | 11/2012 | Hoshino |
| 2012/0300999 A1 | 11/2012 | Bayer |
| 2013/0053646 A1 | 2/2013 | Yamamoto |
| 2013/0057724 A1 | 3/2013 | Miyahara |
| 2013/0066297 A1 | 3/2013 | Shtul |
| 2013/0085329 A1 | 4/2013 | Morrissette |
| 2013/0109916 A1 | 5/2013 | Levy |
| 2013/0116506 A1 | 5/2013 | Bayer |
| 2013/0131447 A1 | 5/2013 | Benning |
| 2013/0137930 A1 | 5/2013 | Menabde |
| 2013/0150671 A1 | 6/2013 | Levy |
| 2013/0169843 A1 | 7/2013 | Ono |
| 2013/0172670 A1 | 7/2013 | Levy |
| 2013/0172676 A1 | 7/2013 | Levy |
| 2013/0197309 A1 | 8/2013 | Sakata |
| 2013/0197556 A1 | 8/2013 | Shelton |
| 2013/0222640 A1 | 8/2013 | Baek |
| 2013/0253268 A1* | 9/2013 | Okada ............... G02B 23/2476 600/104 |
| 2013/0264465 A1 | 10/2013 | Dai |
| 2013/0267778 A1 | 10/2013 | Rehe |
| 2013/0271588 A1 | 10/2013 | Kirma |
| 2013/0274551 A1 | 10/2013 | Kirma |
| 2013/0281925 A1 | 10/2013 | Benscoter |
| 2013/0296649 A1 | 11/2013 | Kirma |
| 2013/0303979 A1 | 11/2013 | Stieglitz |
| 2013/0317295 A1 | 11/2013 | Morse |
| 2014/0018624 A1 | 1/2014 | Bayer |
| 2014/0031627 A1 | 1/2014 | Jacobs |
| 2014/0046136 A1 | 2/2014 | Bayer |
| 2014/0107418 A1 | 4/2014 | Ratnakar |
| 2014/0148644 A1 | 5/2014 | Levi |

(56) References Cited

U.S. PATENT DOCUMENTS

| | | |
|---|---|---|
| 2014/0213850 A1 | 7/2014 | Levy |
| 2014/0225998 A1 | 8/2014 | Dai |
| 2014/0276207 A1 | 9/2014 | Ouyang |
| 2014/0296628 A1 | 10/2014 | Kirma |
| 2014/0296643 A1 | 10/2014 | Levy |
| 2014/0296866 A1 | 10/2014 | Salman |
| 2014/0309495 A1 | 10/2014 | Kirma |
| 2014/0316198 A1 | 10/2014 | Krivopisk |
| 2014/0316204 A1 | 10/2014 | Ofir |
| 2014/0320617 A1 | 10/2014 | Parks |
| 2014/0333742 A1 | 11/2014 | Salman |
| 2014/0333743 A1 | 11/2014 | Gilreath |
| 2014/0336459 A1 | 11/2014 | Bayer |
| 2014/0343358 A1 | 11/2014 | Hameed |
| 2014/0343361 A1 | 11/2014 | Salman |
| 2014/0343489 A1 | 11/2014 | Lang |
| 2014/0364691 A1 | 12/2014 | Krivopisk |
| 2014/0364692 A1 | 12/2014 | Salman |
| 2014/0364694 A1 | 12/2014 | Avron |
| 2015/0005581 A1 | 1/2015 | Salman |
| 2015/0045614 A1 | 2/2015 | Krivopisk |
| 2015/0057500 A1 | 2/2015 | Salman |
| 2015/0094536 A1 | 4/2015 | Wieth |
| 2015/0099925 A1 | 4/2015 | Davidson |
| 2015/0099926 A1 | 4/2015 | Davidson |
| 2015/0105618 A1 | 4/2015 | Levy |
| 2015/0164308 A1 | 6/2015 | Ratnakar |
| 2015/0182105 A1 | 7/2015 | Salman |
| 2015/0196190 A1 | 7/2015 | Levy |
| 2015/0201827 A1 | 7/2015 | Sidar |
| 2015/0208900 A1 | 7/2015 | Vidas |
| 2015/0208909 A1 | 7/2015 | Davidson |
| 2015/0223676 A1 | 8/2015 | Bayer |
| 2015/0230698 A1 | 8/2015 | Cline |
| 2015/0305601 A1 | 10/2015 | Levi |
| 2015/0313445 A1 | 11/2015 | Davidson |
| 2015/0313450 A1 | 11/2015 | Wieth |
| 2015/0313451 A1 | 11/2015 | Salman |
| 2015/0320300 A1 | 11/2015 | Gershov |
| 2015/0342446 A1 | 12/2015 | Levy |
| 2015/0359415 A1 | 12/2015 | Lang |
| 2015/0374206 A1 | 12/2015 | Shimony |
| 2016/0015257 A1 | 1/2016 | Levy |
| 2016/0015258 A1 | 1/2016 | Levin |
| 2016/0058268 A1 | 3/2016 | Salman |

FOREIGN PATENT DOCUMENTS

| | | |
|---|---|---|
| CA | 2812097 | 3/2012 |
| CA | 2798716 | 6/2013 |
| CA | 2798729 | 6/2013 |
| CN | 103348470 | 10/2013 |
| CN | 103403605 | 11/2013 |
| CN | 103491854 | 1/2014 |
| CN | 103702604 | 4/2014 |
| CN | 103732120 | 4/2014 |
| CN | 104717916 | 6/2015 |
| CN | 105246393 | 1/2016 |
| CN | 105324065 | 2/2016 |
| CN | 105324066 | 2/2016 |
| CN | 105338875 | 2/2016 |
| CN | 105358042 | 2/2016 |
| CN | 105358043 | 2/2016 |
| CN | 105377106 | 3/2016 |
| CN | 105407788 | 3/2016 |
| DE | 202010016900 | 5/2011 |
| EP | 1690497 | 8/2006 |
| EP | 1835844 | 9/2007 |
| EP | 1968425 | 9/2008 |
| EP | 1986541 | 11/2008 |
| EP | 1988813 | 11/2008 |
| EP | 2023794 | 2/2009 |
| EP | 2023795 | 2/2009 |
| EP | 2 119 402 A2 | 11/2009 |
| EP | 2190341 | 6/2010 |
| EP | 2211683 | 8/2010 |
| EP | 2457492 | 5/2012 |
| EP | 2457493 | 5/2012 |
| EP | 1988812 | 11/2012 |
| EP | 2520218 | 11/2012 |
| EP | 2604175 | 6/2013 |
| EP | 2618718 | 7/2013 |
| EP | 2635932 | 9/2013 |
| EP | 2648602 | 10/2013 |
| EP | 2649648 | 10/2013 |
| EP | 2672878 | 12/2013 |
| EP | 2736400 | 6/2014 |
| EP | 2744390 | 6/2014 |
| EP | 2442706 | 11/2014 |
| EP | 2865322 | 4/2015 |
| EP | 2908714 | 8/2015 |
| EP | 2979123 | 2/2016 |
| EP | 2991537 | 3/2016 |
| EP | 2994032 | 3/2016 |
| EP | 2994033 | 3/2016 |
| EP | 2994034 | 3/2016 |
| EP | 2996536 | 3/2016 |
| EP | 2996541 | 3/2016 |
| EP | 2996542 | 3/2016 |
| EP | 2996621 | 3/2016 |
| GB | 12196628 | 3/2015 |
| JP | S61126517 A | 6/1986 |
| JP | H1043129 | 2/1998 |
| JP | H10239740 | 9/1998 |
| JP | 11137512 | 5/1999 |
| JP | 2005253543 | 9/2005 |
| JP | 2006025888 | 2/2006 |
| JP | 2006068109 | 3/2006 |
| JP | 2010178766 A | 8/2010 |
| JP | 2012135432 | 7/2012 |
| JP | 2013116277 A2 | 6/2013 |
| JP | 2013123647 | 6/2013 |
| JP | 2013123648 | 6/2013 |
| JP | 2013208459 | 10/2013 |
| JP | 2013215582 | 10/2013 |
| JP | 2013230383 | 11/2013 |
| JP | 2013542467 | 11/2013 |
| JP | 2013544617 | 12/2013 |
| JP | 2014524303 | 9/2014 |
| JP | 2014524819 | 9/2014 |
| JP | 2015533300 | 11/2015 |
| WO | 2006073676 | 7/2006 |
| WO | 2006073725 | 7/2006 |
| WO | 2007070644 | 6/2007 |
| WO | 2007092533 | 8/2007 |
| WO | 2007092636 | 8/2007 |
| WO | 2007087421 | 11/2007 |
| WO | 2007136859 | 11/2007 |
| WO | 2007136879 | 11/2007 |
| WO | 2008015164 | 2/2008 |
| WO | 2009014895 | 1/2009 |
| WO | 2009015396 | 1/2009 |
| WO | 2009049322 | 4/2009 |
| WO | 2009049324 | 4/2009 |
| WO | 2009062179 | 5/2009 |
| WO | 2010146587 | 12/2010 |
| WO | 2012038958 | 3/2012 |
| WO | 2012056453 | 5/2012 |
| WO | 2012075153 A2 | 6/2012 |
| WO | 2012077116 | 6/2012 |
| WO | 2012077117 | 6/2012 |
| WO | 2012096102 | 7/2012 |
| WO | 2012120507 | 9/2012 |
| WO | 2013014673 | 1/2013 |
| WO | 2013024476 | 2/2013 |
| WO | 2014061023 | 4/2014 |
| WO | 2014160983 | 10/2014 |
| WO | 2014179236 | 11/2014 |
| WO | 2014182723 | 11/2014 |
| WO | 2014182728 | 11/2014 |
| WO | 2014183012 | 11/2014 |
| WO | 2014186230 | 11/2014 |
| WO | 2014186519 | 11/2014 |
| WO | 2014186521 | 11/2014 |

(56) References Cited

FOREIGN PATENT DOCUMENTS

| | | |
|---|---|---|
| WO | 2014186525 | 11/2014 |
| WO | 2014186775 | 11/2014 |
| WO | 2014210516 | 12/2014 |
| WO | 2015002847 | 1/2015 |
| WO | 2015047631 | 4/2015 |
| WO | 2015050829 | 4/2015 |
| WO | 2015084442 | 6/2015 |
| WO | 2015095481 | 6/2015 |
| WO | 2015112747 | 7/2015 |
| WO | 2015112899 | 7/2015 |
| WO | 2015134060 | 9/2015 |
| WO | 2015168066 | 11/2015 |
| WO | 2015168664 | 11/2015 |
| WO | 2015171732 | 11/2015 |
| WO | 2015175246 | 11/2015 |
| WO | 2016014581 | 1/2016 |
| WO | 2016033403 | 3/2016 |

OTHER PUBLICATIONS

International Search Report for PCT/US2014/037526, dated Oct. 16, 2014.
International Search Report for PCT/US14/38094, dated Nov. 6, 2014.
International Search Report for PCT/US2015/012751, dated Jun. 26, 2015.
International Search Report for PCT/US2014/58143, dated Jan. 21, 2015.
International Search Report for PCT/US2014/071085, dated Mar. 27, 2015.
International Search Report for PCT/US2015/027902, dated Jul. 23, 2015.
International Search Report for PCT/US2015/012506, dated Dec. 11, 2015.
International Search Report for PCT/US2015/29421, dated Aug. 7, 2015.
International Search Report for PCT/US2015/28962, dated Jul. 28, 2015.
International Search Report for PCT/US2015/47334, dated Dec. 28, 2015.
International Search Report for PCT/US2015/41396, dated Sep. 29, 2015.
International Search Report for PCT/US2015/66486, dated Dec. 17, 2015.
International Search Report for PCT/US2015/6548, dated Feb. 26, 2016.
Office Action dated Feb. 26, 2016 for U.S. Appl. No. 14/274,323.
Office Action dated Feb. 4, 2016 for U.S. Appl. No. 14/271,234.
Corrected Notice of Allowance dated Apr. 13, 2016 for U.S. Appl. No. 13/680,646.
Notice of Allowance dated Mar. 28, 2016 for U.S. Appl. No. 13/413,059.
Notice of Allowance dated Mar. 29, 2016 for U.S. Appl. No. 13/680,646.
Office Action dated Mar. 23, 2016 for U.S. Appl. No. 13/713,449.
Office Action dated Mar. 24, 2016 for U.S. Appl. No. 13/212,627.
Office Action dated Mar. 28, 2016 for U.S. Appl. No. 13/119,032.
Office Action dated May 25, 2016 for U.S. Appl. No. 14/271,234.
Office Action dated May 5, 2016 for U.S. Appl. No. 14/278,338.
Office Action dated May 6, 2016 for U.S. Appl. No. 14/263,896.

* cited by examiner

TUBED MANIFOLD OF A MULTIPLE VIEWING ELEMENTS ENDOSCOPE

CROSS-REFERENCE TO RELATED APPLICATIONS

The present specification relies on, for priority, U.S. Patent Provisional Application No. 62/099,846, entitled "Tubed Manifold of a Multiple Viewing Elements Endoscope" and filed on Jan. 5, 2015, which is herein incorporated by reference in its entirety.

The present specification relates to U.S. patent application Ser. No. 14/469,492, entitled "Manifold for A Multiple Viewing Elements Endoscope", filed on Aug. 26, 2014, which is herein incorporated by reference in its entirety, along with the priority applications listed therein.

The present specification relates to U.S. patent application Ser. No. 13/413,252, entitled "Multi Camera Endoscope Assembly Having Multiple Working Channels", filed on Mar. 6, 2012, which is herein incorporated by reference in its entirety, along with the priority applications listed therein.

FIELD

The present specification relates generally to endoscopy systems and more particularly, to a tubed manifold of a multiple viewing elements endoscopy system and, still more particularly, to an improved manifold comprising a groove for detachably holding a working channel tube.

BACKGROUND

Endoscopes have attained great acceptance within the medical community since they provide a means for performing procedures with minimal patient trauma while enabling the physician to view the internal anatomy of the patient. Over the years, numerous endoscopes have been developed and categorized according to specific applications, such as cystoscopy, colonoscopy, gastroscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle which sometimes includes an ocular for direct viewing. Viewing is also usually possible via an external screen. Various surgical tools may be inserted through a working channel in the endoscope for performing different surgical procedures.

Endoscopes, such as but not limited to, colonoscopes, gastroscopes, and bronchoscopes, that are currently being used typically have a front camera for viewing the internal organ, such as the colon, an illuminator, a fluid injector for cleaning the camera lens and sometimes also the illuminator, and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics which transmits light, generated remotely, to the endoscope tip section. The use of light-emitting diodes (LEDs) for illumination is also known.

Typically, endoscopes use a fluid channeling component or manifold comprising a drilled-through working channel. Such a machine drilled-through channel is often challenging to create with respect to the required high quality of its internal surface in terms of smoothness. A machine drilled-through channel is also less amenable to seamless directional transition of the channel. Repeated insertion of medical/surgical instruments through the working channel may cause deterioration of the internal surface of the channel due to scratches, dents, nicks and the like. A damaged machine-drilled working channel cannot be replaced or repaired and hence the only recourse in such cases is a replacement of the manifold or of the entire tip section of the endoscope.

There is thus a need in the art for endoscopes, such as but not limited to, colonoscopes, gastroscopes, and bronchoscopes, that provide a working channel tube that is detachably or removably positioned within a manifold to define a working channel. The working channel tube is amenable to being easily replaced, retaining a high quality of its internal surface and having seamless directional change/transitions.

SUMMARY

The following embodiments and aspects thereof are described and illustrated in conjunction with systems, tools and methods, which are meant to be exemplary and illustrative, not limiting in scope. The present specification discloses numerous embodiments.

In some embodiments, a manifold for use in a tip section of a multi-viewing elements endoscope is provided.

The present specification discloses a manifold for use in a tip section of a multi-viewing elements endoscope, the manifold comprising: a first section having a first width and a first length and comprising a proximal socket having an entry port and an exit port and a first fluidically isolated conduit there between; an elongated second section attached to said proximal section and having a second width and a second length and comprising a distal socket having an entry port and an exit port and a second fluidically isolated conduit there between, wherein the second width is less than the first width and the second length is more than the first length; a groove comprising a first portion extending from the entry port of the distal socket to the exit port of the proximal socket along a first axis parallel to a longitudinal axis of the manifold, and a second portion extending from the entry port of the proximal socket to the exit port of the proximal socket along a second axis tilted at an angle to the first axis; and a tube having a proximal end and a distal end and positioned in said groove, wherein said distal end is held within the second fluidically isolated conduit and said proximal end is held within the first fluidically isolated conduit, wherein a distal segment of the tube ending in the distal end extends along said first axis to lie within said first portion of the groove, and wherein a proximal segment of the tube ending in the proximal end extends along said second axis to lie in said second portion of the groove.

Optionally, the proximal end of the tube extends beyond the proximal socket.

The proximal end of the tube may be glued or laser welded to the proximal socket and the distal end of the tube may be glued or laser welded to the distal socket.

Optionally, the proximal socket is partially open at an external surface of said manifold. Still optionally, a portion of the groove extending from the exit port of the proximal socket and an entry port of the distal socket is partially open along said external surface of said manifold.

Optionally, the distal and proximal segments are respectively first and second separate tube segments attached together at a predefined angle. The first and second separate tube segments may be glued or laser welded together at a predefined angle.

Optionally, the tube has a circular cross-section.

A diameter of the tube may range from 1 millimeter to 6.5 millimeters or from 1 millimeter to 10.5 millimeters.

Optionally, the tube is made from a medical grade material which may include one or more of stainless steel, brass, and Teflon.

Optionally, the tube is autoclavable.

Optionally, the tube is replaceable in the manifold.

The proximal end of the tube may be connected to a channel that runs from a handle through an elongated shaft and a bending section of the multi-viewing elements endoscope. The channel may be defined by a tube.

The present specification also discloses a multi-viewing elements endoscope comprising a manifold for use in a tip section of the endoscope, the manifold comprising: a first section having a first width and a first length and comprising a proximal socket; an elongated second section attached to said proximal section and having a second width and a second length and comprising a distal socket, wherein the second width is less than the first width and the second length is more than the first length; a groove comprising a first portion extending from an exit port of the distal socket to an exit port of the proximal socket along a first axis parallel to a longitudinal axis of the manifold, and a second portion extending from an entry port of the proximal socket to the exit port of the proximal socket along a second axis tilted at an angle to the first axis; and a tube having a proximal end and a distal end and positioned in said groove, wherein said distal end is held within the distal socket and said proximal end extends out of the proximal socket, wherein a first segment of the tube ending in the distal end extends along said first axis to lie within said first portion of the groove, and wherein a second segment of the tube ending in the proximal end extends along said second axis to lie in said second portion of the groove.

Optionally, the first and second segments are respectively first and second separate tube segments attached together at a predefined angle.

Optionally, the tube has a circular cross-section.

A diameter of the tube may range from 1 millimeter to 6.5 millimeters or from 1 millimeter to 10.5 millimeters.

Optionally, the tube is made from a medical grade material.

Optionally, the tube is autoclavable.

Optionally, the tube is replaceable in the manifold.

The proximal end of the tube may be connected to a channel that runs from a handle through an elongated shaft and a bending section of the endoscope. The channel may be defined by a tube.

The present specification also discloses a method of using an endoscope having a fluid channeling component with detachable working tube, wherein said fluid channeling component comprises a proximal socket, a groove, and a distal socket, said method comprising the steps of: obtaining said endoscope with said fluid channeling component; inserting said detachable working tube through an endoscope working channel and through said proximal socket, groove, and distal socket of said fluid channeling component; performing an endoscopic procedure which includes the insertion of one or more tools through said working tube; removing said working tube through said distal socket, groove, and proximal socket of said fluid channeling component and through said endoscope working channel after said endoscopic procedure; and cleaning or discarding said working tube.

The aforementioned and other embodiments of the present shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION

An aspect of some embodiments relates to an improved fluid channeling component, chassis or manifold for use in a tip section of a multi-viewing elements endoscope. According to an embodiment, the improved manifold of the present specification comprises a groove configured or adapted to position a working channel tube therein. The working channel tube defines a working/service channel of the endoscope.

In one embodiment, the working channel tube is detachable or removable from the manifold and may also be autoclavable. Accordingly, the working channel tube can either be replaced or repaired.

According to an aspect of various embodiments, since the working channel tube is fabricated separately from the manifold, the tube is amenable to an improved quality of its internal surface, provides a continuous path with minimal angulation, and includes smooth and seamless connections and transitions between working channel components.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

As used herein, the indefinite articles "a" and "an" mean "at least one" or "one or more" unless the context clearly dictates otherwise.

It is noted that the term "endoscope" as mentioned to herein may refer particularly to a colonoscope, according to some embodiments, but is not limited only to colonoscopes. The term "endoscope" may refer to any instrument used to examine the interior of a hollow organ or cavity of the body.

Figure 1:
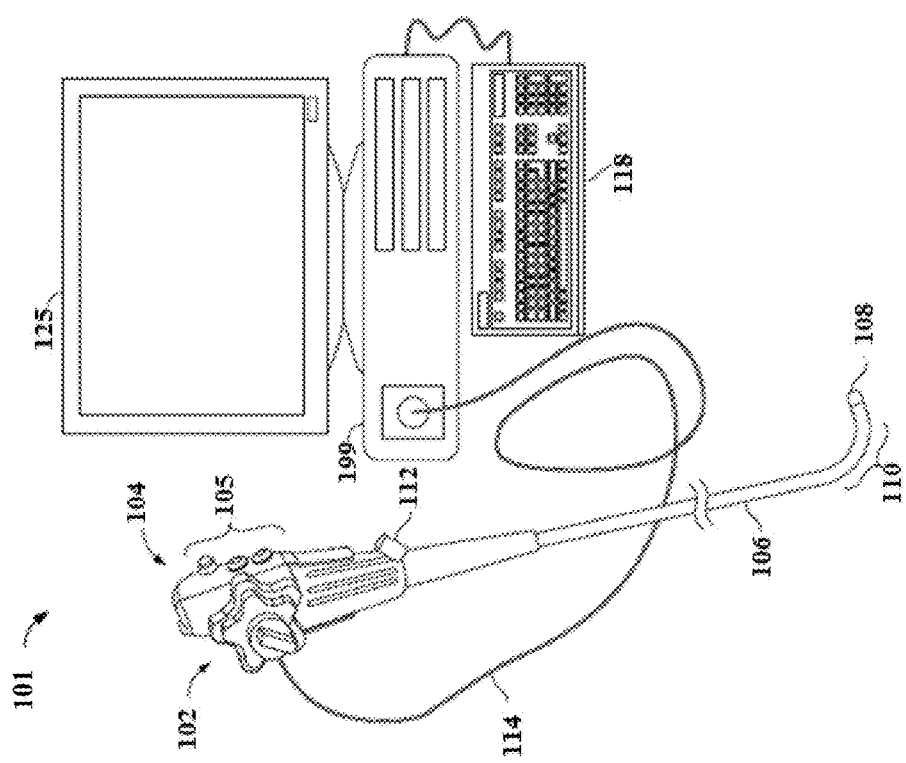
FIG. 1 shows a semi-pictorial view of a multiple viewing elements endoscopy system, according to some embodiments.

Reference is now made to FIG. 1, which shows a multiple viewing elements endoscopy system 101. System 101 may include a multiple viewing elements endoscope 102. Multiple viewing elements endoscope 102 may include a handle 104, from which an elongated shaft 106 emerges. Elongated shaft 106 terminates with a tip section 108 which is turnable by way of a bending section 110. Handle 104 may be used for maneuvering elongated shaft 106 within a body cavity. The handle 104 may include one or more buttons and/or knobs and/or switches 105 which control bending section 110 as well as functions such as fluid injection and suction. Handle 104 may further include at least one, and in some embodiments, one or more working channel openings 112 through which surgical tools may be inserted as well as one and more side service channel openings.

A utility cable 114, also referred to as an umbilical tube, may connect between handle 104 and a main control unit 199. Utility cable 114 may include therein one or more fluid channels and one or more electrical channels. The electrical channel(s) may include at least one data cable for receiving video signals from the front and side-pointing viewing elements, as well as at least one power cable for providing electrical power to the viewing elements and to the discrete illuminators.

The main control unit 199 contains the controls required for displaying the images of internal organs captured by the endoscope 102. The main control unit 199 may govern power transmission to the endoscope's 102 tip section 108, such as for the tip section's viewing elements and illuminators. The main control unit 199 may further control one or more fluid, liquid and/or suction pump(s) which supply corresponding functionalities to the endoscope 102. One or more input devices 118, such as a keyboard, a touch screen and the like may be connected to the main control unit 199 for the purpose of human interaction with the main control unit 199. In the embodiment shown in FIG. 1, the main control unit 199 comprises a screen/display 125 for displaying operation information concerning an endoscopy procedure when the endoscope 102 is in use. The screen 125 may be configured to display images and/or video streams received from the viewing elements of the multi-viewing elements endoscope 102. The screen 125 may further be operative to display a user interface for allowing a human operator to set various features of the endoscopy system.

Optionally, the video streams received from the different viewing elements of the multiple viewing elements endoscope 102 may be displayed separately on at least one monitor (not shown) by uploading information from the main control unit 199, either side-by-side or interchangeably (namely, the operator may switch between views from the different viewing elements manually). Alternatively, these video streams may be processed by the main control unit 199 to combine them into a single, panoramic video frame based on an overlap between fields of view of the viewing elements. In an embodiment, two or more displays may be connected to the main control unit 199, each for displaying a video stream from a different viewing element of the multiple viewing elements endoscope 102. The main control unit 199 is described in U.S. patent application Ser. No. 14/263,896, entitled "Video Processing in a Compact Multi-Viewing Element Endoscope System", and filed on Apr. 28, 2014, which is herein incorporated by reference in its entirety.

Figure 2A:
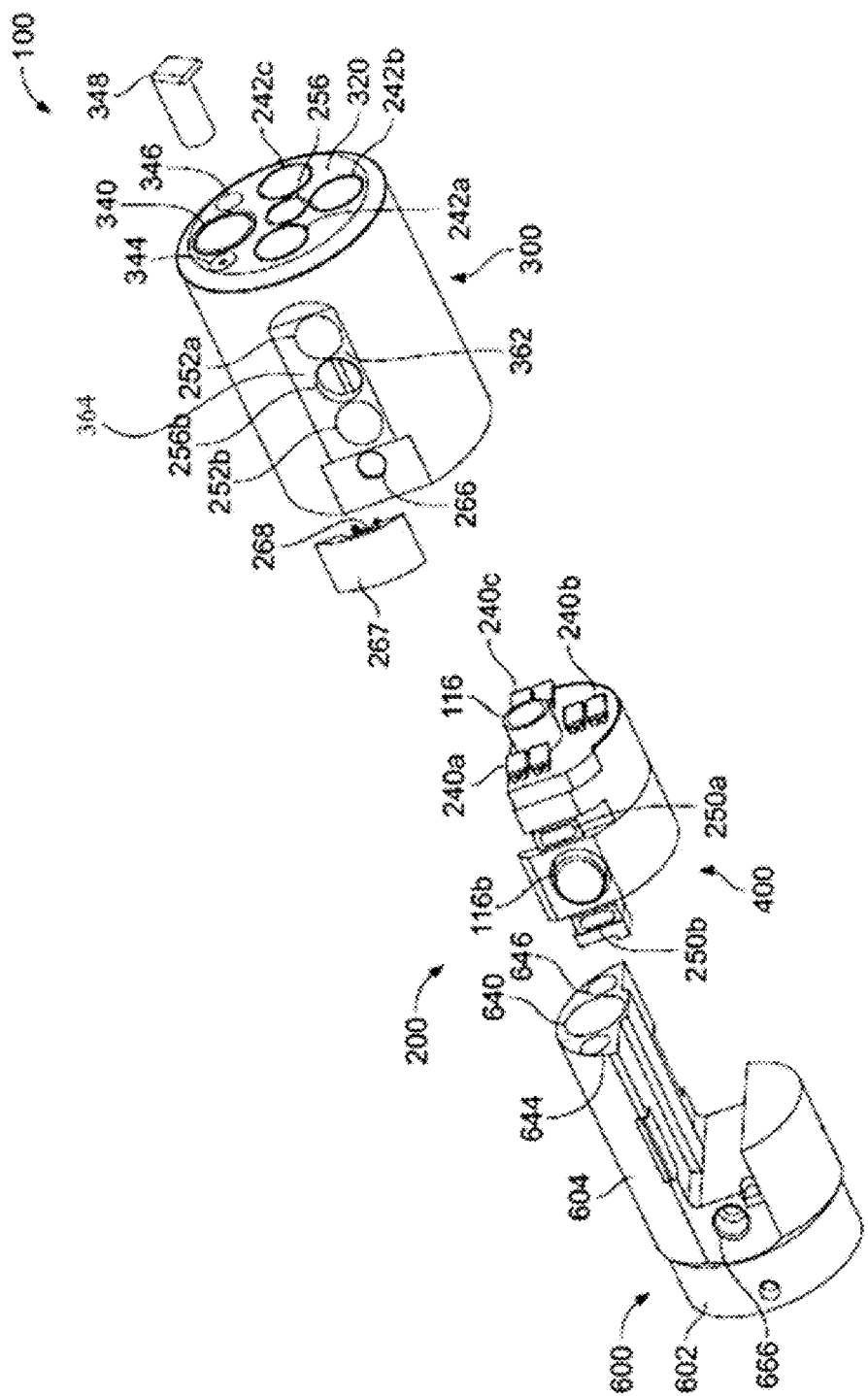
FIG. 2A shows an exploded perspective view of a tip section of a multiple viewing elements endoscope according to some embodiments.

FIG. 2A shows an exploded view of a tip section 200 of a multiple viewing elements endoscope assembly 100 comprising a front working/service channel, according to various embodiments. An aspect of some embodiments also relates to endoscope assembly 100 having the tip section 200 equipped with one or more front working/service channels and one or more side working/service channels (not shown). Accordingly, in an embodiment, tip section 200 of the endoscope 100 may include a tip cover 300, an electronic circuit board assembly 400 and a fluid channeling component 600.

Figure 2B:
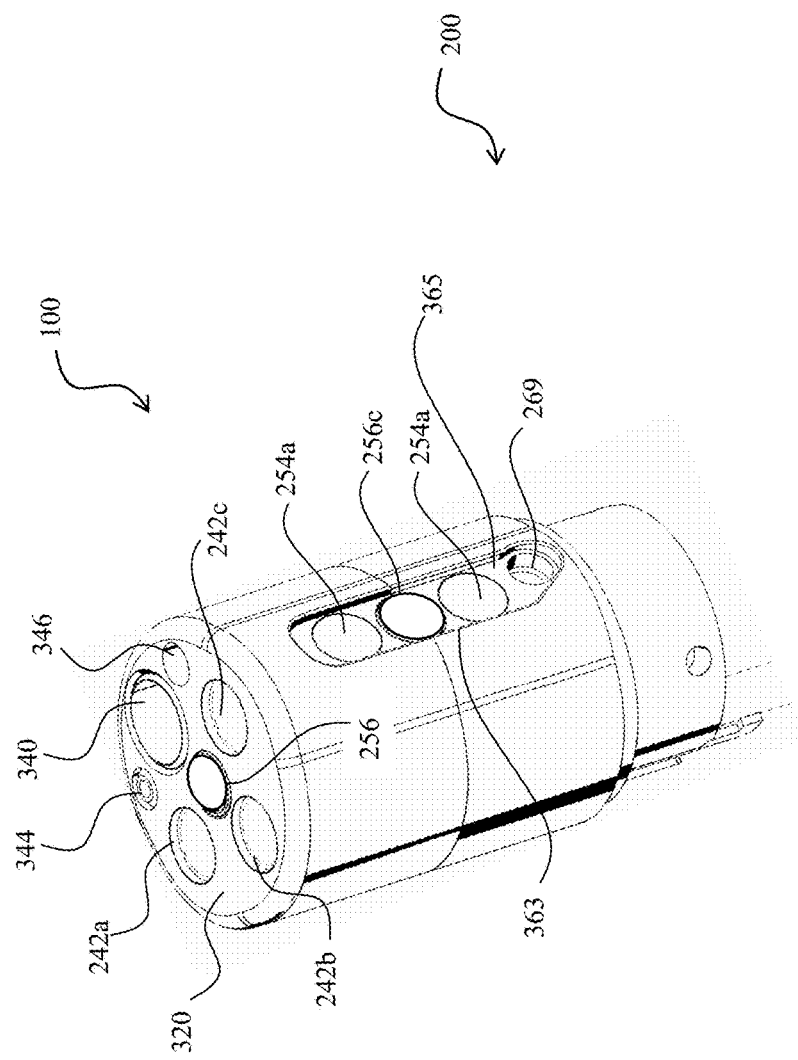
FIG. 2B shows an assembled perspective side view of the tip section of the multiple viewing elements endoscope of FIG. 2A according to some embodiments.
Figure 2C:
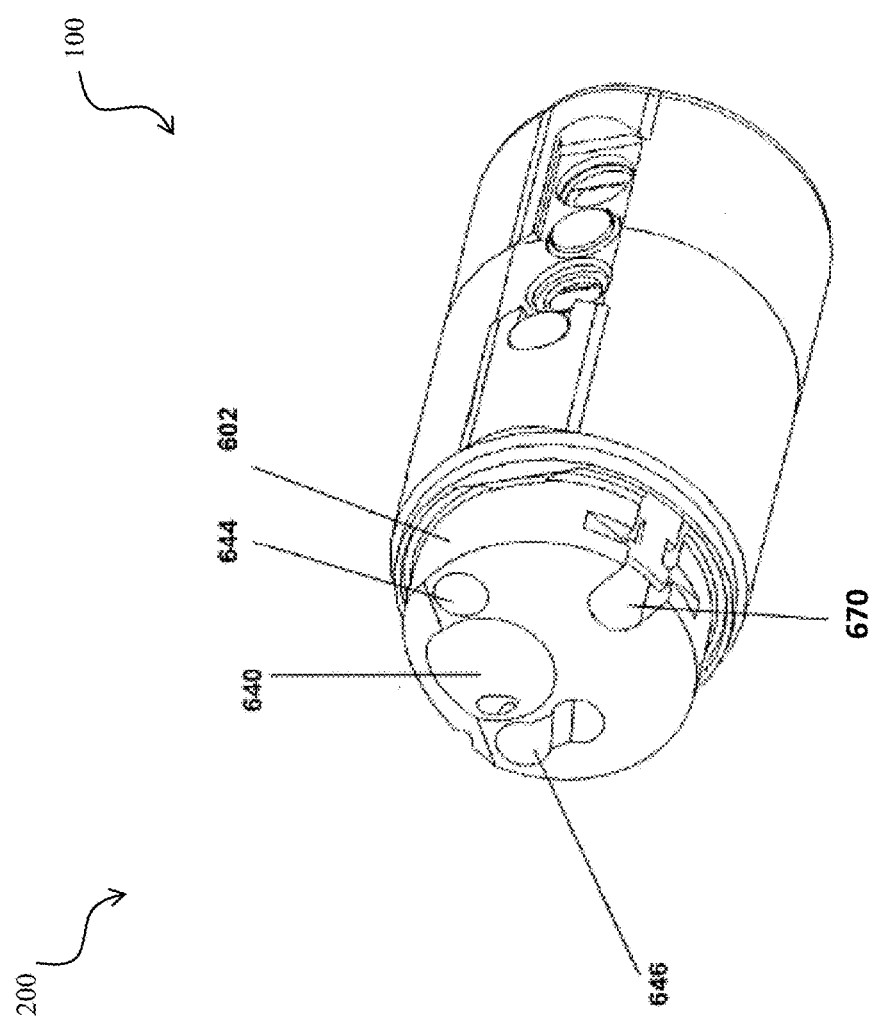
FIG. 2C shows an assembled perspective rear view of the tip section of the multiple viewing elements endoscope of FIG. 2A according to some embodiments.

FIGS. 2B and 2C show assembled perspective views of the tip section 200 of the multiple viewing element endoscope assembly 100 according to an embodiment. Referring to FIGS. 2A through 2C simultaneously, according to some embodiments, the tip section 200 includes a front panel 320 which comprises four quadrants defined by a vertical axis passing through a center of the front panel 320 and a horizontal axis passing through the center, wherein the four quadrants include a top left quadrant, a top right quadrant, a bottom left quadrant and a bottom right quadrant. In various embodiments, a transparent surface, window, or opening to front optical lens assembly 256 (of front looking camera or viewing element 116) is positioned on the front panel 320. In various embodiments, a first front optical window 242b, for a first front illuminator 240b, is positioned on the front panel 320, at least partially within the bottom right quadrant and at least partially within the bottom left quadrant. In various embodiments, a second front optical window 242a, for a second front illuminator 240a, is positioned on the front panel 320, at least partially within the bottom left quadrant. In various embodiments, a third front optical window 242c, for a third front illuminator 240c, is positioned on the front panel 320, at least partially within the bottom right quadrant.

In various embodiments, a front working channel opening 340, for working channel 640, is positioned on the front panel 320, along the vertical axis and at least partially within the top left quadrant and partially within the top right quadrant. In various embodiments, a fluid injector opening 346, for a fluid injector channel 646, is positioned on the front panel 320, at least partially within the top right quadrant. In various embodiments, a nozzle 348 is included which may be aimed at front optical lens assembly 256 and configured for injecting fluid to wash contaminants such as blood, feces and other debris from a surface of front optical lens assembly 256 of front looking camera or viewing element 116. The fluid may include gas which may be used for inflating a body cavity. Optionally, nozzle 348 may be configured for cleaning both front optical lens assembly 256 and optical windows 242a, 242b and/or 252c. In various embodiments, a jet channel opening 344, for a jet channel 644, is positioned on the front panel 320, at least partially within the top left quadrant.

Figure 2D:
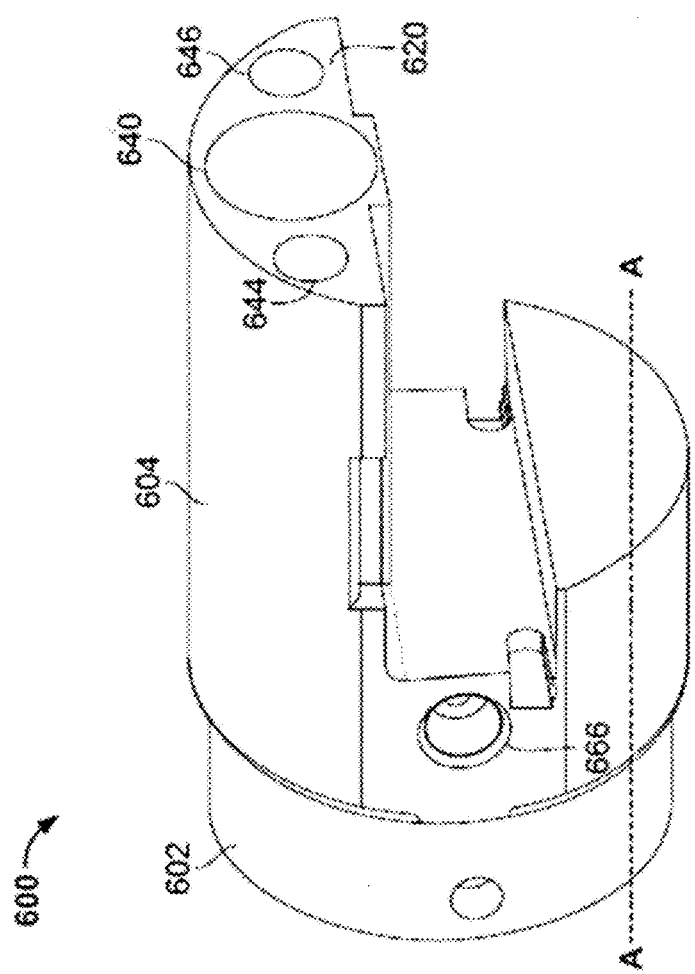
FIG. 2D shows a perspective view of a fluid channeling component of the multiple viewing elements endoscope of FIG. 2A according to an embodiment.

Reference is now made to FIGS. 2A and 2C along with FIG. 2D, which shows a perspective view of the fluid channeling component 600 of the endoscope assembly 100 according to an embodiment. According to some embodiments, fluid channeling component 600 may include a proximal fluid channeling section 602 (or base) which may have an essentially cylindrical shape and a unitary distal channeling section 604 (or elongated housing). Distal fluid channeling section 604 may partially continue the cylindrical shape of proximal fluid channeling section 602 and may have a shape of a partial cylinder (optionally elongated partial cylinder). Distal fluid channeling section 604 may have only a fraction of the cylinder (along the height or length axis of the cylinder) which ends in a distal face 620, wherein another fraction of the cylinder (along the height or length axis of the cylinder) is missing. In other words, in various embodiments, proximal fluid channeling section 602 has a greater width than distal fluid channeling section 604. Distal fluid channeling section 604 may be integrally formed as a unitary block with proximal fluid channeling section 602. The height or length of distal fluid channeling section 604 may by higher or longer than the height or length of proximal fluid channeling section 602. In the embodiment comprising distal fluid channeling section 604, the shape of the partial cylinder (for example, partial cylinder having only a fraction of a cylinder shape along one side of the height axis) may provide a space to accommodate electronic circuit board assembly 400.

Distal fluid channeling section 604 includes working channel 640, which may be configured for insertion of a surgical tool, for example, to remove, treat and/or extract for biopsy a sample or the entirety of the object of interest found in the colon. Distal fluid channeling section 604 further includes jet fluid channel 644 which may be configured for providing a high pressure jet of fluid, such as water or saline, for cleaning the walls of the body cavity (such as the colon) and optionally for suction. Distal fluid channeling section 604 further includes injector channel 646, which may be used for injecting fluid (liquid and/or gas) to wash contaminants such as blood, feces and other debris from a surface of front optical lens assembly 256 of forward-looking viewing element 116 and from the surfaces of the side optical lens assemblies 256b and 256c of side-looking viewing element 116b and an opposite side-looking viewing element, respectively. Proximal fluid channeling section 602 of fluid channeling component 600 also includes side injector channel 666, which may be connected to side injector opening 266, and another side injector channel on the opposite side, which connects to a similar side injector opening positioned on the opposite side of the tip section 200. The proximal fluid channeling section 602 also includes a groove 670 (FIG. 2C) which is adapted to guide (and optionally hold in place) an electric cable(s) which may be connected at its distal end to the electronic components such as viewing elements (for example, cameras, sensors) and/or light sources in the endoscope's tip section. The electric cable(s) delivers electrical power and/or command signals to the tip section and/or transmits video signal from the cameras to be displayed to the user.

Referring back to FIGS. 2A through 2C, electronic circuit board assembly 400 may be configured to carry a front looking viewing element 116, a first side looking viewing element and a second side viewing element 116b which may be similar to front looking viewing element 116 and may include a Charge Coupled Device (CCD) or a Complementary Metal Oxide Semiconductor (CMOS) image sensor. The electronic circuit board assembly 400 may be configured to carry front illuminators 240a, 240b, 240c, which may be associated with front looking viewing element 116 and may be positioned to essentially illuminate the field of view of front looking viewing element 116.

In addition, electronic circuit board assembly 400 may be configured to carry side illuminators 250a and 250b, which may be associated with side looking viewing element 116b and may be positioned to essentially illuminate side looking viewing element's 116b field of view. Electronic circuit board assembly 400 may also be configured to carry side illuminators which may be associated with the opposite side looking viewing element and which may be similar to side illuminators 250a and 250b.

Front illuminators 240a, 240b, 240c and side illuminators 250a and 250b may optionally be discrete illuminators and may include a light-emitting diode (LED), which may be a white light LED, an infrared light LED, a near infrared light LED, an ultraviolet light LED or any other LED.

The term "discrete", concerning discrete illuminator, may refer to an illumination source, which generates light internally, in contrast to a non-discrete illuminator, which may be, for example, a fiber optic merely transmitting light generated remotely.

Tip cover 300 may be configured to fit over the inner parts of the tip section 200 including electronic circuit board assembly 400 and fluid channeling component 600 and to provide protection to the internal components in the inner parts. Front optical lens assembly 256 may include a plurality of lenses, static or movable, which may provide a field of view of 90 degrees or more, 120 degrees or more or up to essentially 180 degrees. Front optical lens assembly 256 may provide a focal length in the range of about 3 to 100 millimeters. The term focal length may be used to refer to the distance from a lens to a sensor or may be used to refer to the distance, from the lens, over which an object remains in focus. One of ordinary skill in the art would understand what definition for focal length is being used based on the context and distances discussed. An optical axis of front looking camera or viewing element 116 may be essentially directed along the long dimension of the endoscope. However, since front looking camera or viewing element 116 is typically a wide angle camera, its field of view may include viewing directions at large angles to its optical axis.

Visible on the sidewall 362 of tip cover 300 is a depression 364 wherein placed within the depression 364 is a side optical lens assembly 256b for side looking camera or viewing element 116b, which may be similar to front optical lens assembly 256, and optical windows 252a and 252b of illuminators 250a and 250b for side looking camera or viewing element 116b. On sidewall 363 of tip cover 300, on the opposing side to side optical lens assembly 256b, is a depression 365 and an optical lens assembly 256c for another side looking camera, which may be similar to side optical lens assembly 256b, and optical windows 254a and 254b for another set of illuminators similar to illuminators 250a and 250b. The side optical lens assemblies 256b, 256c may provide a focal length in the range of about 3 to 100 millimeters. In another embodiment, tip section 200 may include only one side viewing element.

An optical axis of the first side viewing element 116b may be essentially directed perpendicular to the long dimension of the endoscope. An optical axis of the second side viewing element may be essentially directed perpendicular to the long dimension of the endoscope. However, since each side viewing element typically comprises a wide angle camera, its field of view may include viewing directions at large angles to its optical axis. In accordance with some embodiments, each side viewing element has a field of view of 90 degrees or more, 120 degrees or more or up to essentially 180 degrees.

In addition, side injector opening 266 of side injector channel 666 may be located at a distal end of sidewall 362 and side injector opening 269 of an opposite side injector may be located at a proximal end of sidewall 363. A nozzle cover 267 may be configured to fit side injector opening 266 and a similar nozzle cover (not shown) may be configured to fit side injector opening 269.

Additionally, nozzle cover 267 may include a nozzle 268 which may be aimed at side optical lens assembly 256b and configured for injecting fluid to wash contaminants such as blood, feces and other debris from a surface of side optical lens assembly 256b of side looking camera or viewing element 116b. The fluid may include gas which may be used for inflating a body cavity. Optionally, nozzle 268 may be configured for cleaning both side optical lens assembly 256b and optical windows 252a and/or 252b.

It is noted that according to some embodiments, although tip section 200 is presented herein showing one side thereof, the opposing side may include elements similar to the side elements described herein (for example, side looking camera, side optical lens assembly, injector(s), nozzle(s), illuminator(s), window(s), opening(s) and other elements).

The fluid channeling component, chassis or manifold 600 is characterized in that the working channel 640 is a machine drilled-through conduit, passage or pathway. An improved fluid channeling component or manifold of the present specification is characterized in that the working channel is a standalone tube fabricated separately from the manifold and thereafter fitted, assembled or secured therein. In accordance with an embodiment, the tubed manifold of the present specification replaces the fluid channeling chassis/manifold 600 within the tip section 200 of FIG. 2A while the tip cover 300 and the electronic circuit board assembly 400 remain the same.

Figure 3A:
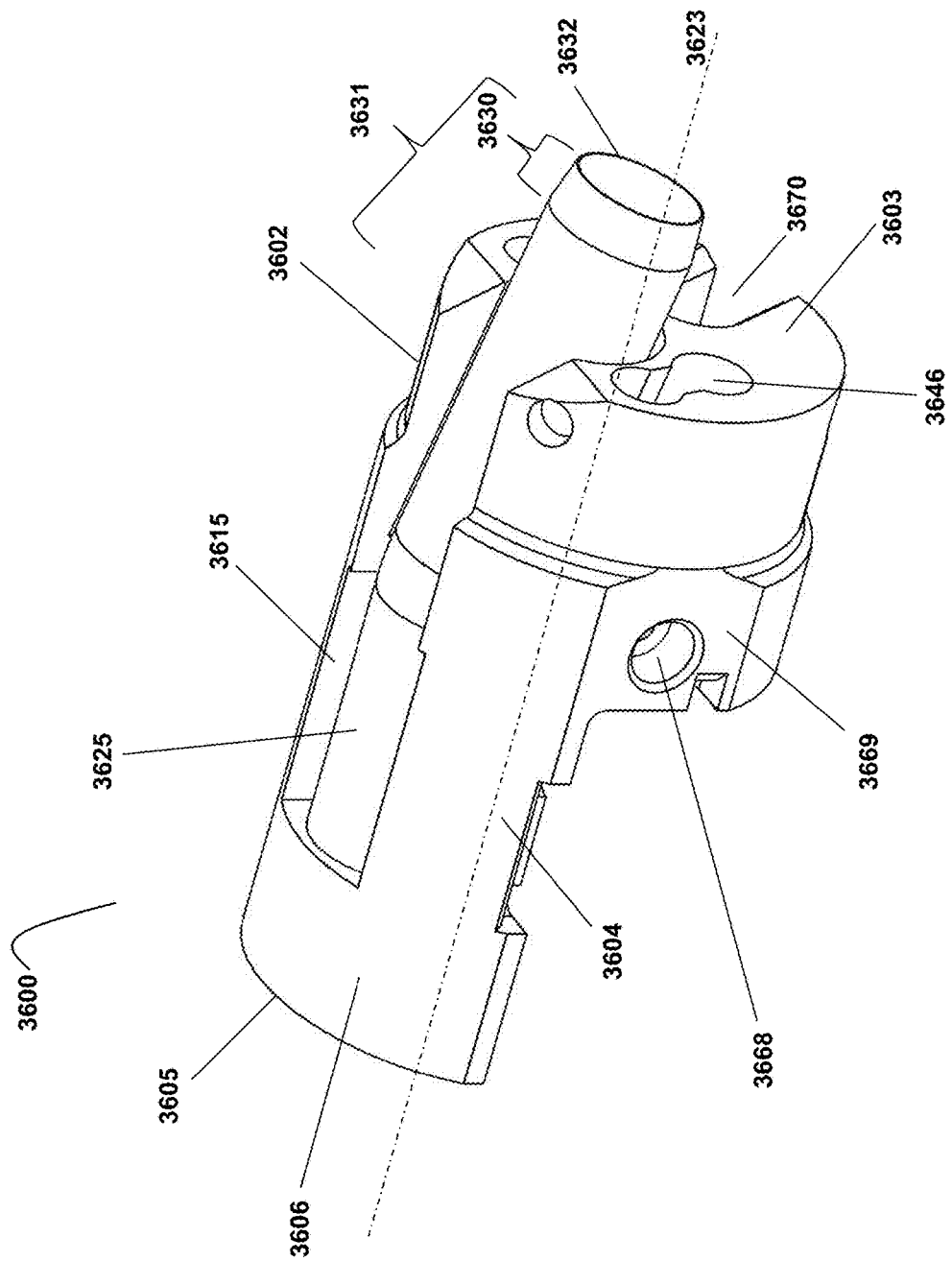
FIG. 3A shows a perspective view of a tubed fluid channeling component, chassis or manifold accommodating a working/service channel tube in accordance with an embodiment of the present specification.
Figure 3B:
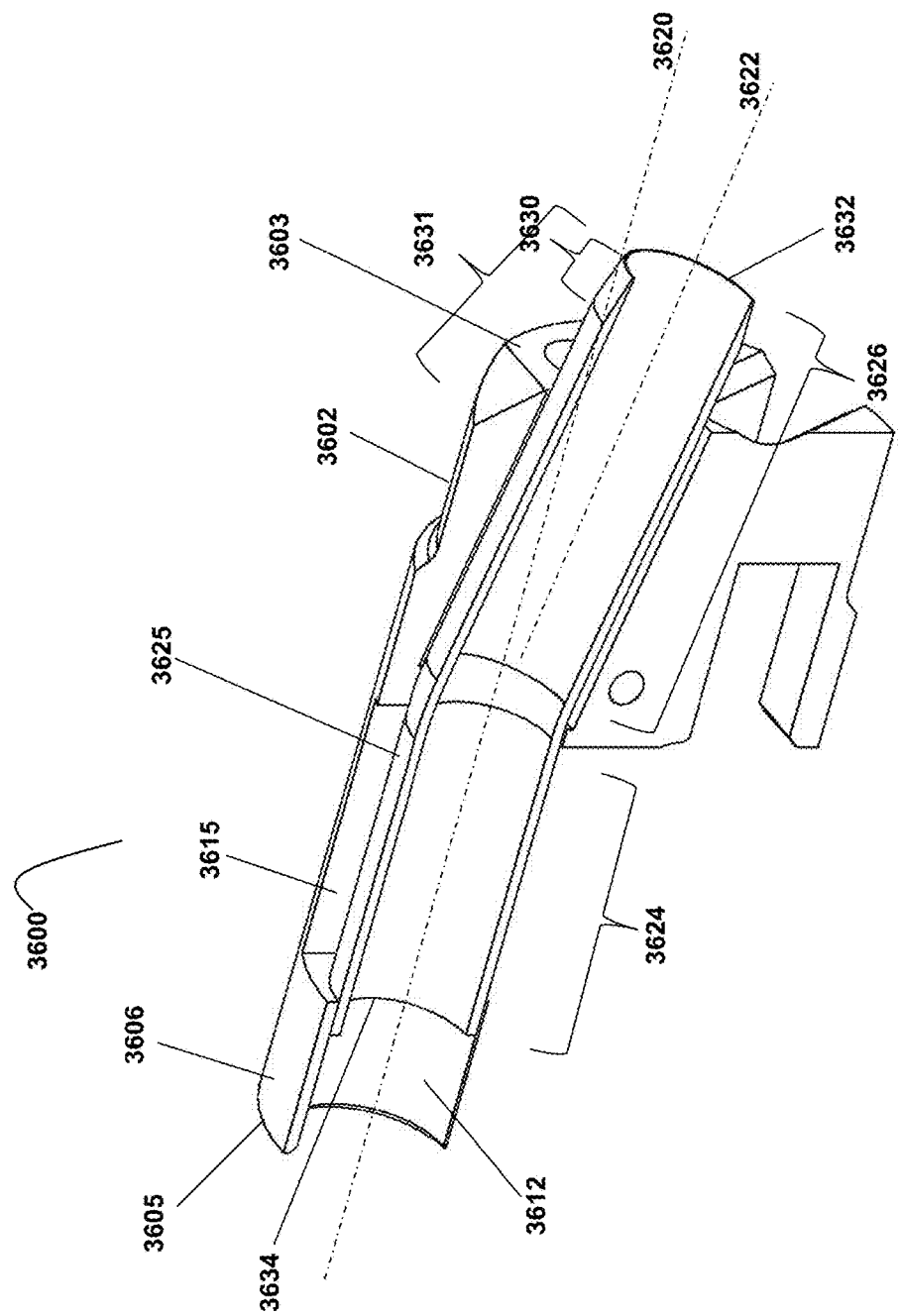
FIG. 3B is a vertical cross-section view of the tubed fluid channeling component or manifold of FIG. 3A.
Figure 3C:
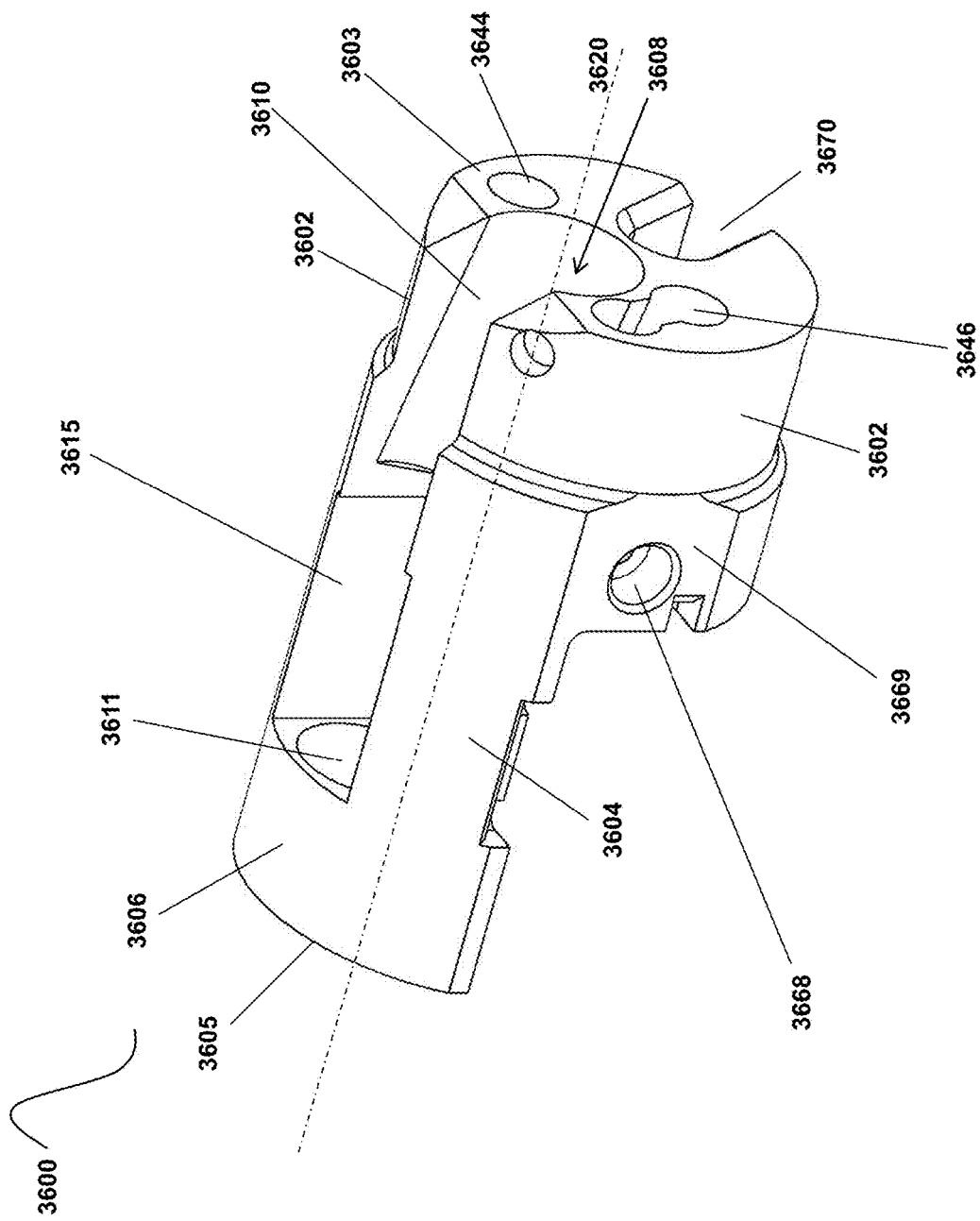
FIG. 3C is another perspective view of the tubed fluid channeling component or manifold of FIG. 3A with the working/service channel tube removed.
Figure 3D:
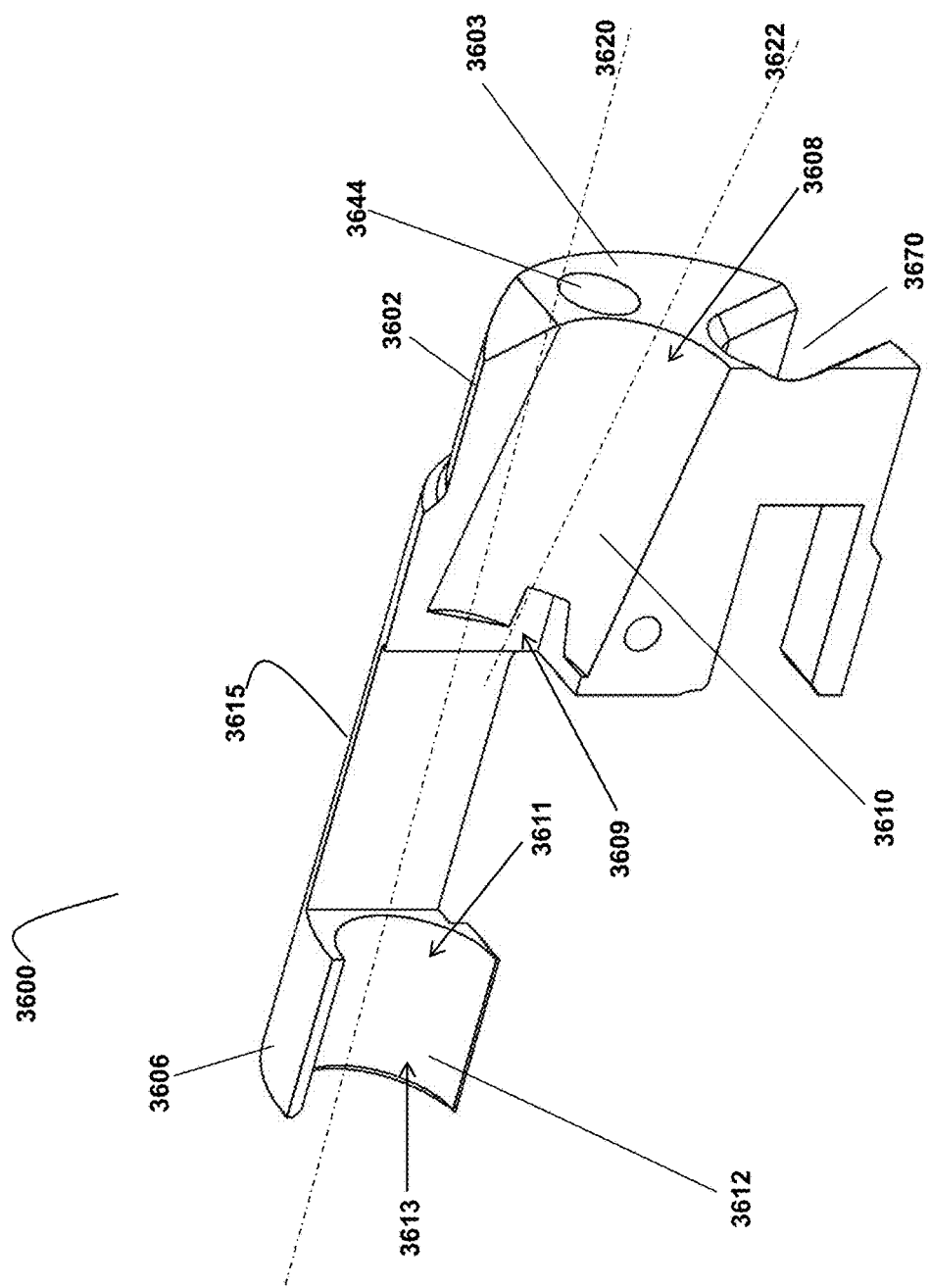
FIG. 3D is vertical cross-section view of the tubed fluid channeling component or manifold of FIG. 3A with the working/service channel tube removed.

FIG. 3A shows a perspective view of a tubed fluid channeling component, chassis or manifold 3600 accommodating a working/service channel tube 3625 in accordance with an embodiment of the present specification; FIG. 3B is a vertical cross-section view of the tubed fluid channeling component or manifold 3600 of FIG. 3A; FIG. 3C is another perspective view of the tubed fluid channeling component or manifold 3600 of FIG. 3A with the working/service channel tube removed; and FIG. 3D is vertical cross-section view of the tubed fluid channeling component or manifold 3600 of FIG. 3A with the working/service channel tube removed.

Referring now to FIGS. 3A through 3D simultaneously, the tubed fluid channeling component or manifold 3600 includes a first fluid channeling/manifold section 3602 (or base) which has an essentially cylindrical shape and a second fluid channeling/manifold section 3604 (or elongated housing). Second fluid channeling/manifold section 3604 partially continues the cylindrical shape of first fluid channeling/manifold section 3602 and has a shape of a partial cylinder (optionally, elongated partial cylinder). Second fluid channeling section 3604 comprises only a fraction of the cylinder (along a length axis of the cylinder, the length axis being parallel to a longitudinal axis 3623), wherein the other fraction of the cylinder (along the length axis of the cylinder) is missing, as the shape of the partial cylinder (that is, the partial cylinder having only a fraction of a cylinder shape along one side of the length axis) of the second fluid channeling section 3604 provides a space to accommodate the electronic circuit board assembly 400 of FIG. 2A. In some embodiments, first fluid channeling section 3602 has a greater width than second fluid channeling section 3604 to allow for openings for fluid and electronic components such as injector channel 3646 and electrical cable opening 3670, described below. In an embodiment, first fluid channeling section 3602 has a diameter that is substantially equal to that of the distal tip, ranging from 7 mm to 17 mm, and any increment therein. In an embodiment, second fluid channeling section 3604 comprises approximately ⅓ of the distal tip diameter, or from 2 mm to 6 mm and any increment therein. In one embodiment, second fluid channeling section 3604 is integrally formed as a unitary block with first fluid channeling section 3602. In some embodiments, the length of second fluid channeling section 3604 is longer than the length of first fluid channeling section 3602. In some embodiments, the relative lengths of first fluid channeling section 3602 and second fluid channeling section 3604 are designed to produce a distal tip that has the shortest length possible to allow for increased maneuverability of the scope during a medical procedure, while allowing for front and side viewing elements and associated illuminators as described above, which influence the overall length of the distal tip.

A distal end 3605 of fluid channeling component 3600 includes a distal depression, socket, hollow area, area to receive a plug or area to receive a housing 3612 having an entry port 3611 and an exit port 3613, where exit port 3613 is closer to distal end 3605 than entry port 3611. A proximal end 3603 of fluid channeling component 3600 includes a proximal depression, socket, hollow area, area to receive a plug or area to receive a housing 3610 having an entry port 3608 and an exit port 3609 defining, in one embodiment, a through-hole or fluidically isolated conduit there between.

Referring to FIGS. 2A and 3C, the proximal socket 3610 is positioned within the first portion 3602 of the manifold 3600, which is more cylindrical in shape than the second portion 3604. Further, a working channel (as described above) enters the distal tip section through the first proximal portion 3602 which is at an angle (approximately 0 to 10 degrees) relative to the longitudinal length of the manifold and follows through to the second distal portion 3604 which is at approximately 0 degrees relative to the longitudinal length of the manifold. Thus, the primal socket is placed in the slightly angled or tilted portion of the manifold.

In some embodiments, the diameter of the opening or hole of the socket is adapted to the working channel diameter. In some embodiments, the diameter of the opening or hole of the socket ranges from 0.5 mm to 8 mm.

In various embodiments, the tubed fluid channeling component or manifold 3600 is partially open along its external surface. A longitudinal groove 3615, formed in the manifold 3600, extends from at least a portion of the proximal socket 3610 to the distal socket 3612. In an embodiment, the length of the longitudinal groove 3615 ranges from 0.05 mm to 15.0 mm.

In various embodiments, groove 3615 comprises a first portion that extends between the exit port 3609 (of the proximal socket 3610) and the entry port 3611 (of the distal socket 3612) along a first axis 3620 and a second portion that extends between the entry port 3608 (of the proximal socket 3610) and exit port 3609 (of the proximal socket 3610) along a second axis 3622 tilted at an angle to the first axis 3620. In one embodiment, the first axis 3620 is parallel to a longitudinal axis 3623 of the tubed manifold 3600. Accordingly, the working channel tube 3625 comprises anterior distal segment 3624 lying within the first portion of the groove 3615 along the first axis 3620 and a proximal segment 3626 lying within the second portion of the groove 3615 along the second axis 3622. Thus, the proximal segment 3626 of the working channel tube 3625 is angularly tilted with respect to the distal segment 3624.

It should be noted that the angular tilt between the distal and proximal segments 3624, 3626 results in a bent working channel comprising a directional transition/change at the point of the angular tilt or bent. In some embodiments, the angle between distal and proximal segments 3624 and 3626 ranges from 0 degrees to 10 degrees. Conventional manifolds, such as manifold 600 of FIG. 2A, and specifically shown in FIG. 2D, also comprise a bent working channel since a distal segment of the working channel has to be positioned above a center of the tip section 200 of FIG. 2A in order to bypass the electronic circuit board assembly 400 (FIG. 2A). However, since the working channel in conventional manifolds is machine drilled, the directional transition at the point of the angular tilt or bent is not smooth and seamless. In contrast, the working channel tube 3625 is amenable to be bent with a smooth and seamless transition. Also, since the working channel tube 3625 is fabricated separately from the tubed manifold 3600, accurate and elaborate processes like shaping, lapping and honing of the internal surface of the tube 3625 can be performed. This provides a smoother internal surface of the tube 3625, ensuring a high internal surface quality compared to a machine drilled channel of the conventional manifolds.

In some embodiments, the proximal socket 3610 is open or uncovered at the external surface of the manifold 3600 while the distal socket 3612 is formed as a through-hole (that forms a fluidically isolated conduit) within a distal portion 3606 of the second section 3604 to distal end 3605. In various embodiments, a portion of the groove 3615, extending along the external surface of the manifold from the proximal end 3603 to the entry port 3611 of the distal socket 3612, is open or uncovered.

Proximal end 3603 also includes a jet fluid channel 3644 configured for providing a high pressure jet of fluid, such as water or saline, for cleaning the walls of a body cavity (such as the colon) and optionally for suction. The proximal end 3603 further includes injector channel 3646, which is used for injecting fluid (liquid and/or gas) to wash contaminants such as blood, feces and other debris from a surface of front optical lens assembly 256 of forward-looking viewing element 116 (FIG. 2A). A side wall 3669 (formed within the depression 365, shown in FIG. 2B) may include a side injector channel 3668 which may be connected to a side injector opening of a tip cover. An opening 3670 allows a plurality of electrical cables to be accommodated for supplying power to a plurality of viewing elements and illuminators to a tip section, such as the tip section 200 of the multi-viewing elements endoscope 100 of FIG. 2A.

In accordance with an aspect of the present specification, the proximal socket 3610, the groove 3615 and the distal socket 3612 are configured/adapted to removably accommodate, hold, position or house a working channel tube 3625. As shown in FIG. 3B, the working channel tube 3625 has a proximal end 3632 and a distal end 3634 and defines a working channel within the tubed fluid channeling component or manifold 3600. In one embodiment, the proximal and distal ends 3632, 3634 are additionally laser welded or glued to the respective proximal and distal sockets 3610, 3612. While in one embodiment the working channel tube 3625 has a circular cross-section, in alternate embodiments the cross-section may be square, rectangular, oval or polygonal. In various embodiments, the length of the working channel tube 3625 ranges from 0.08 mm to 25.0 mm. In various embodiments, where the working channel tube 3625 has a circular cross-section, its diameter ranges from 0.5 millimeter to 8 millimeters. In alternate embodiments, where the working channel tube 3625 has a circular cross-section, its diameter ranges from 1 millimeter to 6.5 millimeters. In still further embodiments, where the working channel tube 3625 has a circular cross-section, its diameter ranges from 1 millimeter to 10.5 millimeters. Thus, using working channel tubes of different diameters and correspondingly configured proximal socket 3610, groove 3615 and distal socket 3612 of a plurality of tubed manifolds 3600 can be manufactured that have varying diameters of working channel conduits, thus accommodating for varying sizes of a tip of an endoscope.

In various embodiments, the distal and proximal segments 3624, 3626 are separate tubes that are joined or fused together to form the working channel tube 3625. The two segments are joined, attached or connected using methods such as, but not limited to, gluing, laser/thermal welding, sewing, and tying. In some embodiments, the distal and proximal segments 3624, 3626 are formed by bending a single tube. In various embodiments, the working channel tube 3625 is composed of stainless steel, brass, Teflon or any other medical grade material known to persons of ordinary skill in the art. Since the working channel tube 3625, in accordance with an embodiment, is removable or detachable, it can be advantageously replaced or repaired when the internal surface of the tube 3625 has been damaged, such as dented or scratched, due to surgical instruments being inserted therethrough. It should be noted herein that conventional methods for removing or detaching components that are affixed using laser welding or adhesives are used to remove or detach the working channel tube 3625 of the present specification. The use of a separate working channel tube 3625 in the improved manifold 3600 of the present specification allows for better maintenance of the working channel. In one embodiment, the working channel tube 3625 is autoclavable.

Referring now to FIG. 1 along with FIGS. 3A through 3D, in accordance with an embodiment, an overall working channel of the endoscope comprises a first section defined by the first/working channel tube 3625 within the tubed fluid channeling component or manifold 3600 and a second section defined by a second tube/conduit that runs from the handle 104 and through the elongated shaft 106 and the bending section 110. The second tube is connected or joined to the first tube 3625 at the proximal end 3632. In one embodiment, the second tube overlaps the first tube 3625 protruding beyond the proximal end 3603 of the tubed manifold 3600 (wherein the diameter of the second tube is slightly greater than the diameter of the first tube 3625), forming a transition section 3630 and an overlapping portion 3631 (FIGS. 3A and 3B). Transition section 3630 is used to retain a constant inner diameter of the channel at a transition edge or proximal end 3632 so that the second tube can overlap the first tube 3625. As shown in FIG. 3A, overlapping portion 3631 may enter into proximal section 3602. In some embodiments, overlapping portion 3631 may range between 0.5 mm to 20 mm.

In various embodiments, the two tubes are attached/connected at the overlapping portion 3631 using one or more suitable attachment/connection methods such as gluing, laser/thermal welding, sewing, tying or any other method known to those of ordinary skill in the art. In an alternate embodiment, the second tube is inserted into the first tube 3625 to form the overlapping portion 3631. In this embodiment, the transition edge or proximal end 3632 of the first tube 3625 is expanded by heating (such as using laser as a heating source) so that its diameter is sufficiently extended to accommodate the second tube. On cooling, the proximal end 3632 contracts and shrink fits onto the second tube. Additionally, in one embodiment, the attachment/connection of the two tubes is reinforced through gluing.

Figure 4:
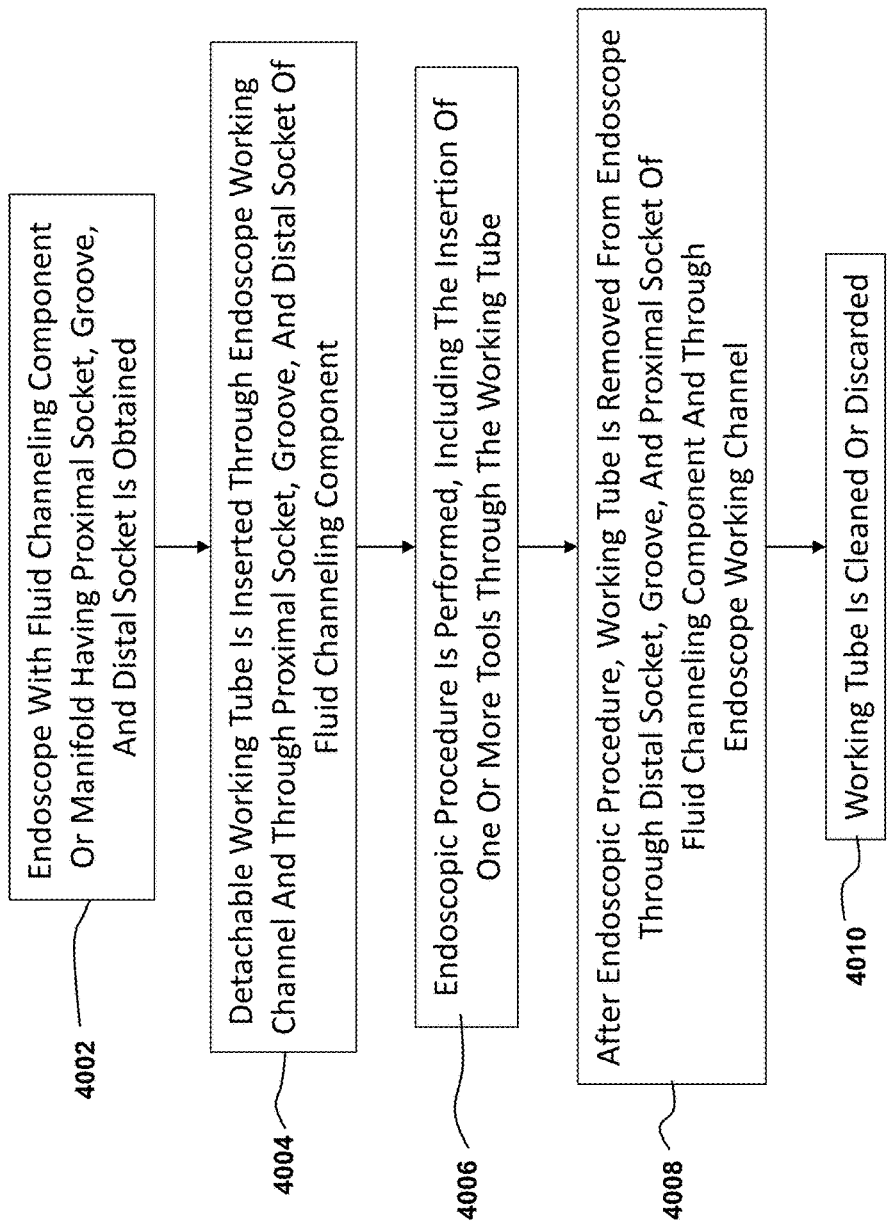
FIG. 4 is a flow chart listing the steps involved in a method of using an endoscope having a fluid channeling component with detachable tube, in accordance with one embodiment of the present specification.

FIG. 4 is a flow chart listing the steps involved in a method of using an endoscope having a fluid channeling component with a detachable tube, in accordance with one embodiment of the present specification. At step 4002, an endoscope with a fluid channeling component or manifold having a proximal socket, groove, and distal socket is obtained. A detachable working tube is inserted through an endoscope working channel and through the proximal socket, groove, and distal socket of the fluid channeling component at step 4004. Then, at step 4006, an endoscopic procedure is performed which includes the insertion of one or more tools through the working tube. After the endoscopic procedure is completed, the working tube is removed from the endoscope through the distal socket, groove, and proximal socket of the fluid channeling component and through the endoscope working channel at step 4008. The working tube is cleaned or discarded at step 4010.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A multi-viewing elements endoscope comprising:
   a manifold positioned in a tip section of the endoscope, the manifold comprising:
      a first section having a first width and a first length, and comprising a proximal socket;
      a second section extending from said first section proximate said proximal socket, and having a second width and a second length, and comprising a distal socket, wherein the second width is less than the first width and the second length is greater than the first length; and
      a groove extending from an entry port of the proximal socket to an entry port of the distal socket, wherein the groove is partially open and extends inward towards a central longitudinal axis of the manifold from an outer circumferential surface of the manifold;
   a tube having a proximal end and a distal end and positioned in said groove, wherein said distal end is held within the distal socket and said proximal end extends out of the proximal socket; and
   an electronic circuit board assembly positioned adjacent said manifold in the tip section, wherein the electronic circuit board assembly comprises a front viewing element and a first side viewing element, and wherein each of the front viewing element and the first side viewing element comprises at least one of a charge coupled device and a complementary metal oxide semiconductor image sensor.

2. The endoscope of claim 1, wherein the tube comprises a first tube segment and a second tube segment that meet each other at a predefined angle.

3. The endoscope of claim 2, wherein the first and the second tube segments are laser-welded, sewn, or glued together at the predefined angle.

4. The endoscope of claim 1, wherein the tube has a circular cross-section.

5. The endoscope of claim 4, wherein a diameter of the tube ranges from 1 millimeter to 10.5 millimeters.

6. The endoscope of claim 1, wherein the tube is made from a medical grade material, stainless steel, brass, and/or Teflon.

7. The endoscope of claim 1, wherein the tube is autoclavable and reusable, or disposable.

8. The endoscope of claim 1, wherein the proximal end of the tube is connected to a channel that runs from a handle through a shaft and a bending section of the endoscope, and wherein said channel is defined by a third tube.

9. The endoscope of claim 1, wherein the proximal end of the tube is glued, laser-welded, or sewn to the proximal socket, and wherein the distal end of the tube is glued, laser-welded, or sewn to the distal socket.

10. The endoscope of claim 1, wherein the proximal socket is partially open at an external surface of said manifold.

11. The endoscope of claim 10, wherein the partial opening of the groove is connected to the partial opening of the proximal socket.

* * * * *